(12) United States Patent
Kreidler

(10) Patent No.: US 9,005,541 B2
(45) Date of Patent: Apr. 14, 2015

(54) MEDICAL STERILIZATION CONTAINER WITH GAS-EXCHANGE FILTER

(75) Inventor: Winfried Kreidler, Tuttlingen (DE)

(73) Assignee: Innovations Medical GmbH, Tuttlingen (DE)

( * ) Notice: Subject to any disclaimer, the term of this patent is extended or adjusted under 35 U.S.C. 154(b) by 952 days.

(21) Appl. No.: 13/176,264

(22) Filed: Jul. 5, 2011

(65) Prior Publication Data

US 2012/0006366 A1    Jan. 12, 2012

(30) Foreign Application Priority Data

Jul. 6, 2010 (DE) .................... 20 2010 009 925 U

(51) Int. Cl.
*A61L 2/20* (2006.01)
*A61L 2/26* (2006.01)
*A61B 19/02* (2006.01)

(52) U.S. Cl.
CPC ............. *A61L 2/26* (2013.01); *A61B 19/026* (2013.01); *A61B 2019/0202* (2013.01); *A61B 2019/0211* (2013.01); *A61L 2202/182* (2013.01); *A61L 2202/24* (2013.01)

(58) Field of Classification Search
USPC .................................. 422/292, 300; 134/198
See application file for complete search history.

(56) References Cited

U.S. PATENT DOCUMENTS 7,381,385 B2    6/2008    Gleichauf et al.

FOREIGN PATENT DOCUMENTS

DE         202 03 984 U1    6/2002
DE         202004002095 U1    4/2004

*Primary Examiner* — Sean E Conley
(74) *Attorney, Agent, or Firm* — McGlew and Tuttle, P.C.

(57) ABSTRACT

A medical sterilization container has a removable container cover, which is provided in a wall area (4) with gas-exchange openings (5), with a filter unit (55) for gas exchange has an interchangeable filter sheet covering the gas-exchange openings (5) on the inside, which is arranged within a ring-shaped circumferential frame element (15) and is held pressably against an inside of the wall area (4) by a pressure washer (36) provided with openings (45). The pressure washer (36) is detachably connected to frame element (15) or the wall area (4) and has a ring groove (48) with a preferably elastic sealing ring (49), which seals the wall area (4) provided with the gas-exchange openings (5) against the frame element (15). To prevent a shifting of and/or damage to the filter sheet during a clamping process, the pressure washer (36) can be pressed against the wall area (4) by a spring washer (35). The spring washer (35) is provided with bayonet connection elements (38) which can be meshed and unmeshed with bayonet catch elements (20) of the frame element (15). The spring washer (35) is rotatable opposite the pressure washer (36) about a common central axis of rotation of the pressure washer (36) and of the spring washer (35).

20 Claims, 5 Drawing Sheets

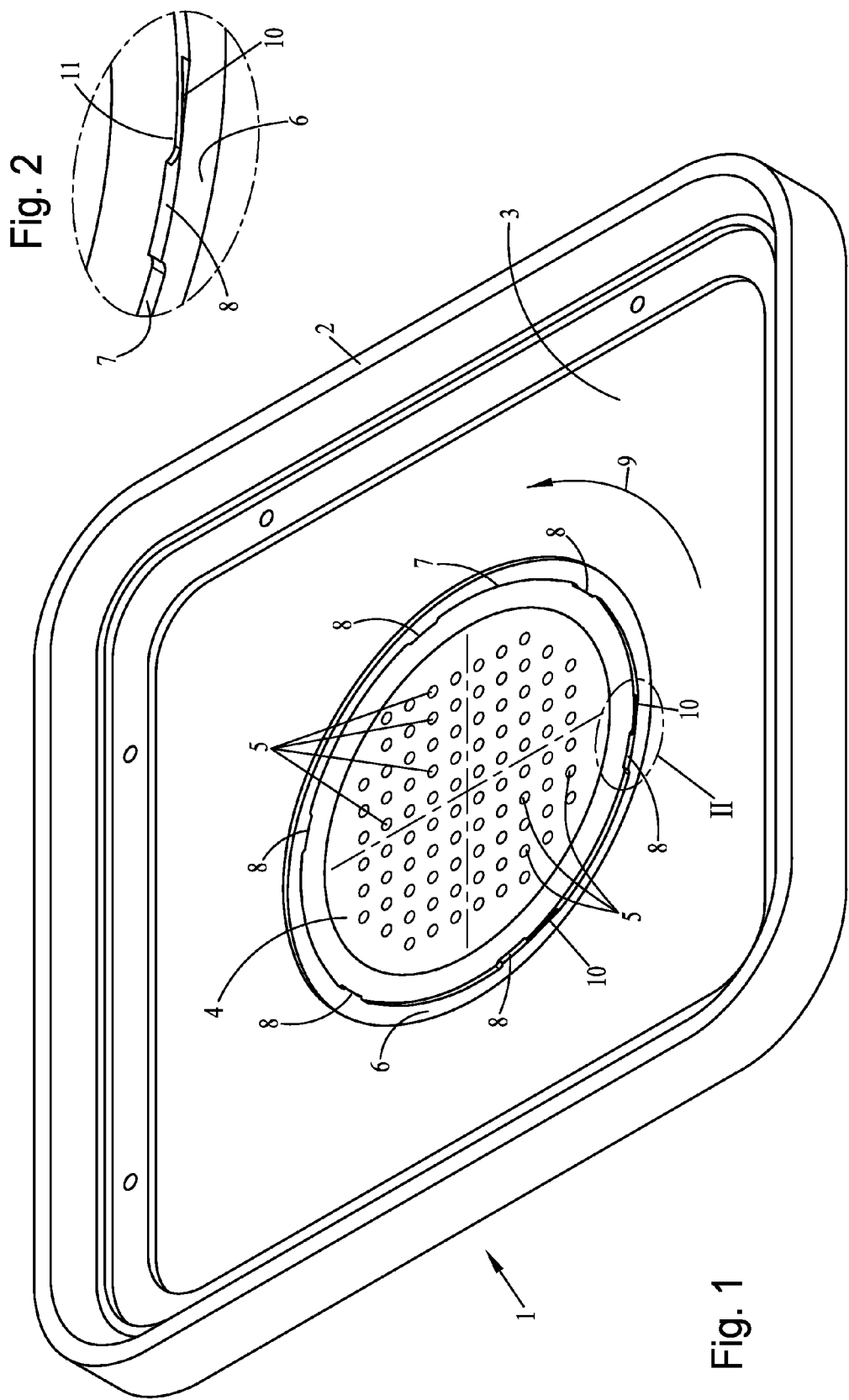

MEDICAL STERILIZATION CONTAINER WITH GAS-EXCHANGE FILTER

CROSS REFERENCE TO RELATED APPLICATIONS

This application claims the benefit of priority under 35 U.S.C. §119 of German Utility Model Application DE 20 2010 009 925.0 filed Jul. 6, 2010, the entire contents of which are incorporated herein by reference.

FIELD OF THE INVENTION

The present invention pertains to a medical sterilization container provided with a removable cover, which is provided in a wall area provided with gas-exchange openings with a filter unit for the gas exchange, which unit has an interchangeable filter sheet covering the gas-exchange openings on the inside, which sheet is arranged within a ring-shaped circumferential frame element and is held pressably against the inside of the wall area by a pressure washer provided with openings, whereby the pressure washer is detachably connected to the frame element or the wall area and has a ring groove with a preferably elastic sealing ring that seals the wall area provided with the gas-exchange openings against the frame element.

BACKGROUND OF THE INVENTION

Sterilization containers of this type are usually used for sterilizing medical instruments. For this, such sterilization containers have a container cover, which is detachably tightly connected to a corresponding lower housing of the sterilization container. In order to guarantee "aeration and ventilation" in closed sterilization containers, such a sterilization container has in one of its wall areas gas-exchange openings, which are covered during operation on the inside by means of a filter sheet. Such a filter sheet usually consists of paper, a nonwoven fabric or textile material. This filter sheet is replaced on a regular basis with increasing duration of operation and/or in case of a change in the instruments to be sterilized.

For this, the filter sheet is held by a pressure washer which meshes detachably with a frame element arranged on the inside at the wall area, surrounding the gas-exchange openings in a ring-shaped manner. The detachable connection between the pressure washer and frame element is established by a bayonet connection, which is formed from bayonet catch elements or from bayonet connection elements, which can be mutually meshed with one another, at the pressure washer, on the one hand, and, at the frame element, on the other hand. To seal the pressure washer against the wall area of the sterilization container or against the frame element, a preferably elastic sealing ring is provided that is mounted on the wall side in a circumferential ring groove of the pressure washer. In the mounted state, the sealing ring presses against the filter sheet, which is preferably inserted—with a relative accuracy of fit—into the ring-shaped frame element. The pressure washer, filter sheet and frame element thus form a type of filter unit.

By means of the bayonet connection formed between the frame element and the pressure washer, the pressure washer may only be released from the frame element by means of a rotating relative motion and can again be meshed with same in a positive-locking manner rotating in the opposite direction. Since the sealing ring of the pressure washer presses tightly against the filter sheet and the pressure washer is accordingly to be braced under axial prestress against the filter sheet especially during insertion, this routinely leads to a shifting of filter sheet and/or to its damage.

SUMMARY OF THE INVENTION

Consequently, a basic object of the present invention is to improve the filter unit of a sterilization container of the type mentioned in the introduction in such a way that the filter sheet is not shifted and/or damage during insertion.

This object is accomplished according to the present invention in that the pressure washer can be pressed by a spring washer against the wall area, and that the spring washer is provided with bayonet connection elements, which can be meshed and unmeshed with bayonet catch elements of the frame element, and that the spring washer can be rotated opposite the pressure washer about a common central axis of rotation of the pressure washer and of the spring washer.

By means of this embodiment of the filter unit according to the present invention, it is guaranteed with certainty that the filter sheet cannot be shifted or damaged during insertion, since the pressure washer pressing the filter sheet against the wall area does not have to be rotated itself for fixing the pressure washer. Both the spring washer and the pressure washer have at least one smooth surface on their sides facing one another, such that the spring washer can be easily rotated in relation to the pressure washer for establishing the bayonet connection. Thus, the spring washer can, however, be pressed with relatively great prestress against the pressure washer and rotated, without the pressure washer also being moved with it. Thus, the advantage is also further achieved that a higher pressing pressure is exerted onto the pressure washer directly or by means of a sealing ring lying on the filter sheet, as a result of which the sealing action of the sealing ring is improved. Such higher pressing forces are not possible in the previously known filter units, since there the pressure washer has to be rotated to establish the bayonet connection and would lead to destruction of the filter sheet due to the direct frictionally engaged contact of its sealing ring with the filter sheet.

According to a further aspect of the invention, provisions can be made that the spring washer is to be provided with openings, which are essentially designed and arranged according to the same surface pattern as the openings of the pressure washer. Provisions are made here that the openings of the pressure washer and the spring washer lie congruently one above the other after establishing the bayonet connection between the spring washer and the frame element. Consequently, a gas exchange that is as large as possible in terms of area is achieved.

According to a further aspect of the invention, provisions can be made that the bayonet connection elements of the spring washer are formed from cam- or tongue-like projections protruding radially outwardly on their circular circumference, which mesh with radial mounting slots or grooves arranged on the inside of the frame element, which are each connected to the insertion expansions of the frame element in a direction of rotation. Due to this arrangement and embodiment of the bayonet connection elements, the spring washer can be simply and securely fastened to the frame element of the wall area and be removed again as well, if necessary. Another advantage is that the bayonet connection elements of the spring washer can be produced in a simple and easy manner. Thus, the entire spring washer can be produced in a uniform punching process, in which both the outer contour and the openings can be produced at the same time.

Furthermore, provisions can be made that the insertion expansions extend over the entire height or thickness of the frame element, and in that the pressure washer is provided on its circumference with radially outwardly protruding, cam- or tongue-like projections, each of which is mounted in such an insertion expansion and secure the pressure washer against rotation. By means of this embodiment, it is especially achieved that the pressure washer in the frame element cannot rotate during the rotation of the spring washer, such that an impairment of the filter sheet "clamped" by the pressure washer is ruled out with certainty.

Further, a further aspect of the invention, provisions may be made that the frame element has a circumferential ring land protruding axially towards the wall area, which ring land meshes with a ring groove of the wall area and is detachably connected to the ring groove via a bayonet connection. By means of this embodiment of the present invention, the frame element can be fastened to the wall area easily and with certainty and can also be removed, if necessary, for example, for cleaning purposes.

According to a further aspect of the invention, provisions may further be made that the pressure washer and spring washer are essentially the same size, consist of metal or plastic and lie on top of one another within the frame element essentially in a congruent position of their openings. By means of this embodiment, it is especially possible to insert the pressure washer and spring washer together into the frame element after inserting the filter sheet.

According to a further aspect of the invention, provisions may be made that the spring washer lies axially elastically on the pressure washer in the mounted state and is concentrically rotatably centered on the spring washer by means of a central axial connection. Also by means of this embodiment, the spring washer and the pressure washer can be inserted together into the frame element and can be connected to same in line with the function thereof. By means of the central axial connection, a centering between the pressure washer and the spring washer is achieved, such that these cannot be shifted radially against one another during insertion in or removal from the frame element. Due to the axial, elastic "lying" of the spring washer on the pressure washer, a continuously active spring pressure with a reliable seal is guaranteed, on the one hand, a manual pressing pressure that is too strong is prevented, on the other hand. Thus, too high, harmful pressure forces cannot be exerted onto the pressure washer and thus onto the filter sheet during the insertion of the spring washer.

Furthermore, provisions may be made according to a further aspect of the invention that the spring washer is provided on its top side with at least one fixed gripping part. By means of this embodiment according to the present invention, the spring washer can be handled in an extremely simple manner. The gripping part here can be arranged centrally on the spring washer. If the common axial connection is also provided, then the spring washer and the pressure washer can be handled via this gripping part together for replacing the filter sheet in an extremely simple manner.

To be able to apply the necessary force or the necessary torque to the frame element when inserting the frame element into the ring groove of the wall area, the ring-shaped frame element is provided on the top side with at least two essentially diametrically opposed positive-locking elements. With these positive-locking elements, a manually actuatable hand lever can be nonrotatably and detachably meshed in a positive-locking manner. The user is thus enabled in a simple manner to produce a fixed, stable bayonet connection between the frame element and the wall area and to cancel this connection again if this should be necessary, for example, for cleaning purposes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a bottom perspective of a container cover according to the invention;

FIG. 2 is an enlarged detail II of the ring groove of the container cover from FIG. 1;

DESCRIPTION OF THE PREFERRED EMBODIMENTS

Figure 3:
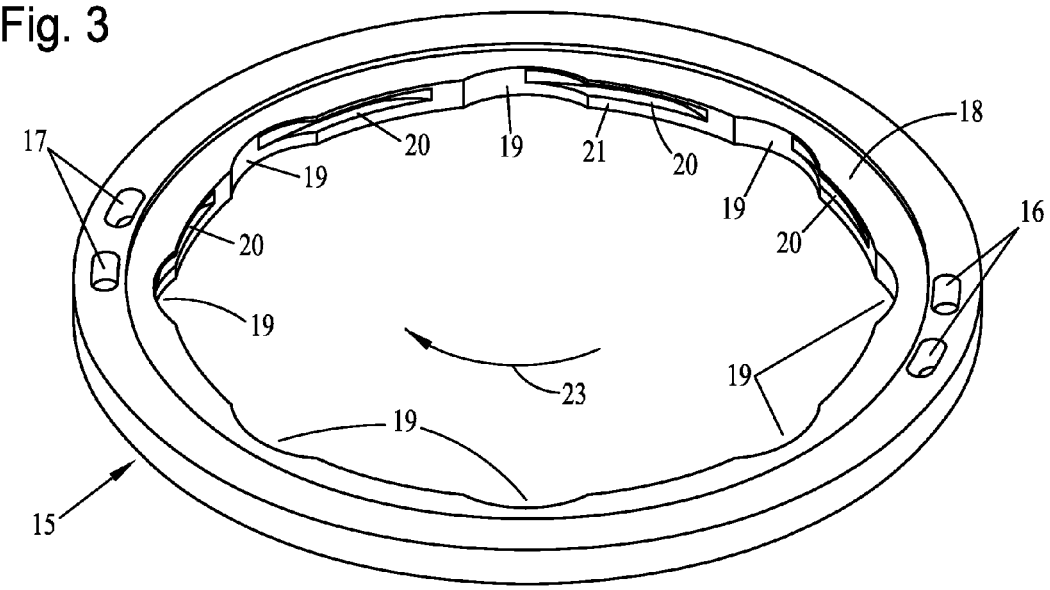
FIG. 3 is a perspective view of a frame element that can be meshed with the ring groove of the container cover from FIG. 1.

Referring to the drawings in particular, FIG. 1 shows, in an exemplary manner, an embodiment variant of a container cover 1, which has a rectangular, rounded basic shape. Such a container cover 1 can be placed during operation tightly onto a corresponding container bottom part, which, however, is not shown in the drawing. This container cover 1 forms, with this container bottom part, a medical sterilization container, which is used, for example, to sterilize medical instruments.

As is evident from FIG. 1, the container cover 1 has a circumferential edge flange 2 that encloses a preferably flat wall element 3 of the container cover 1. Furthermore, a seal is usually provided in the mounted state of the container cover 1 on a container bottom part, such that the container cover 1 can be mounted tightly on the bottom part. Furthermore, it is evident from FIG. 1 that the wall element 3 has a central wall area 4, which in the present exemplary embodiment is provided with a plurality of gas-exchange openings 5. During operation, a gas exchange with the environment takes place through these gas-exchange openings, for example, during the heating or cooling of the entire sterilization container. In this wall area 4, a ring groove 6 with a ring-shaped design is provided on the inside. This ring groove 6 is provided with recesses 8 directed radially inwards in the area of its circumferential inner edge 7. As is especially evident from FIG. 2, a locking slot 10, which is covered accordingly by a fixing flange 11, opens into each of these recesses 8. FIG. 2 shows an enlarged view of the area II from FIG. 1 in this regard.

Figure 4:
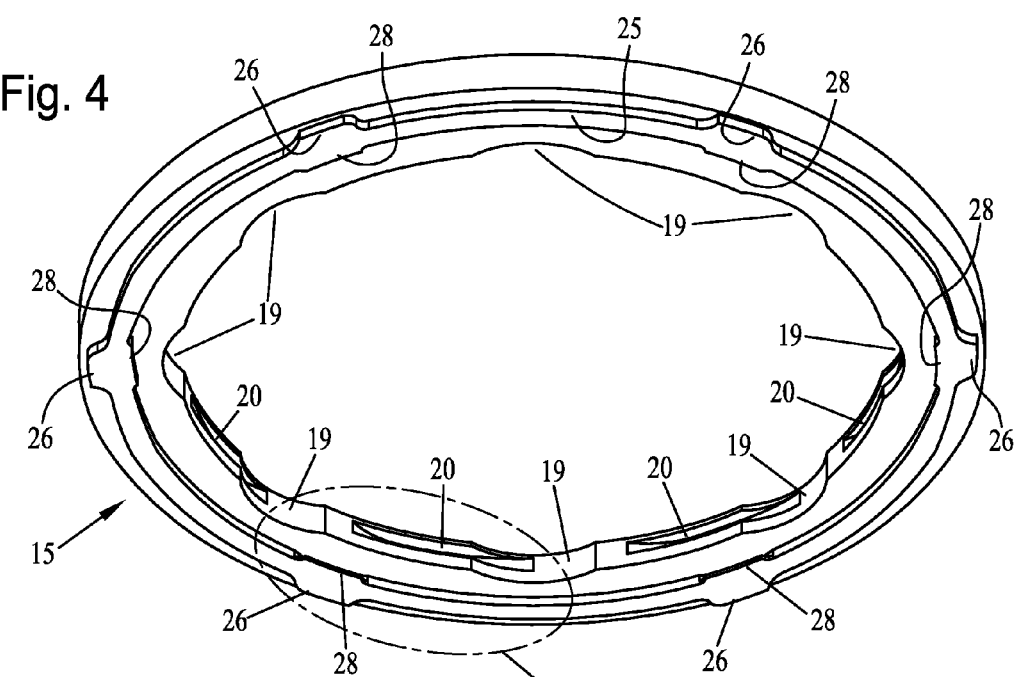
FIG. 4 is a second perspective view showing the frame element from FIG. 3, in which the ring land that can be meshed with the ring groove of the container cover can be seen.
Figure 5:
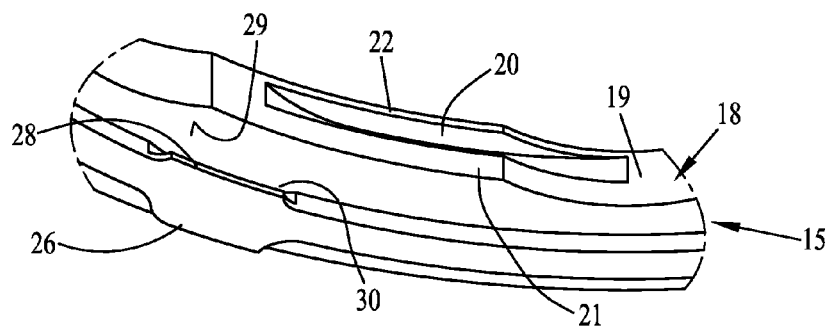
FIG. 5 is an enlarged detail V of the frame element from FIG. 4.

A frame element 15 which is shown in an exemplary manner in FIGS. 3 through 5 can be inserted into the ring groove 6 of the wall element 3 or of the wall area 4. For this, FIG. 3 shows a type of top view, while FIG. 4 shows a bottom view of this frame element 15.

It can be seen from FIG. 3 that the frame element 15 has a ring-shaped design and on the top side has positive locking elements 16 and 17 arranged next to each other in pairs. These positive-locking elements 16 and 17 lie essentially diametrically opposed and are each designed like an elongated hole in the present exemplary embodiment. These positive-locking elements 16 and 17 can be meshed with a hand lever in a positive-locking and detachable manner in order to be able to adjust the frame element by rotating in a simple manner.

Furthermore, the frame element 15 forms a radially inwards protruding, completely circumferential holding flange 18, which is provided on the inside with insertion expansions 19 arranged distributed uniformly on the circumference. In the circumferential holding flange 18, each of these insertion expansions 19 thus forms a radial expansion running in an arc-shaped manner, whose function will be explained in detail later.

A mounting groove extending over a partial circumference of the frame element 15 that is defined, on the one hand, on the bottom side by a flange element 21 and, on the other hand, on the top side by another flange element 22, opens into each of these insertion expansions 19. These insertion expansions 19, together with the mounting grooves 20 extending in the circumferential direction, form a part of a bayonet connection for detachably holding a spring washer, as will be explained later.

FIG. 5 shows especially for this an enlarged detail V from FIG. 4, in which one of the insertion expansions 19 together with the associated mounting groove 20 as well as the two flange elements 21 and 22 can be seen in detail.

It is easily conceivable that, for example, a washer with radially protruding connection elements can be axially inserted into the insertion expansions 19 and subsequently can be rotated in the direction of arrow 23 and can thus be meshed in a fixed manner with the mounting grooves 20 in the manner of a bayonet connection.

Further, it is evident from FIG. 4 that the frame element 15, on the bottom side, forms an axially protruding ring land 25, with which the frame element 15 can be inserted into the ring groove 6 of the container cover 1 from FIG. 1. In the present exemplary embodiment, this ring land 25 forms a plurality of centering elements distributed uniformly on the circumference and lying on a greater diameter, with which the ring land 25 can be inserted concentrically into the ring groove 6 of the container cover 1 of FIG. 1. In a corresponding embodiment of the ring groove 6, these centering elements 26 with the ring groove also form a type of bayonet connection.

In the present exemplary embodiment, the ring land 25 of the frame element 15 has in the area of its inner edge 27 a plurality of holding flanges 28 arranged uniformly on the circumference, which are used for the fixed and detachable holding of the frame element 15 in the ring groove of the wall element 3. Accordingly, these holding flanges 28 can each be meshed in a positive-locking manner with one of the locking slots 10 of the ring groove 6 of the container cover 1.

For this, it can be seen, in particular, from the enlarged partial view of FIG. 5 that these holding flanges 28 have such a distance to the bottom side 29 of the inner circumferential holding flange 18 that a clearance 30 is formed between the respective holding flange 28 and this bottom side 29 for receiving the respectively assigned fixing flange 11 of the ring groove 6.

It is now easily conceivable that, in a corresponding angle orientation, the frame element 15 can be axially inserted into the recesses 8 of the ring groove 6 with its radially inwards directed holding flanges 28 of its ring land 25. Here, the holding flanges 28 reach, in the axial direction, the same plane as the locking slots 10 described with regard to FIG. 2. By rotating the entire frame element 15 in the direction of arrow 9, the holding flanges are inserted into the locking slots 10, so that a type of bayonet connection is formed between the frame element 15 and the ring groove 6 or the container cover 1. Thus, in case of a corresponding direction of rotation opposite to arrow 9, the frame element 15 is again detachable from the locking slots 10 and can be removed from the inside of the container cover 1, for example, for cleaning purposes.

In the present exemplary embodiment, this frame element 15 is used to lock or hold a filter sheet in a clamped manner, as is still explained in detail later especially with regard to FIGS. 12 and 13.

In order to fix such a filter sheet that completely covers the entire wall area 4 with its gas-exchange openings 5 of the container cover 1 (FIG. 1) interchangeably in this wall area 4, a spring washer 35 (FIG. 6) as well as a pressure washer 36 (FIG. 7) are provided according to the present invention.

Figure 6:
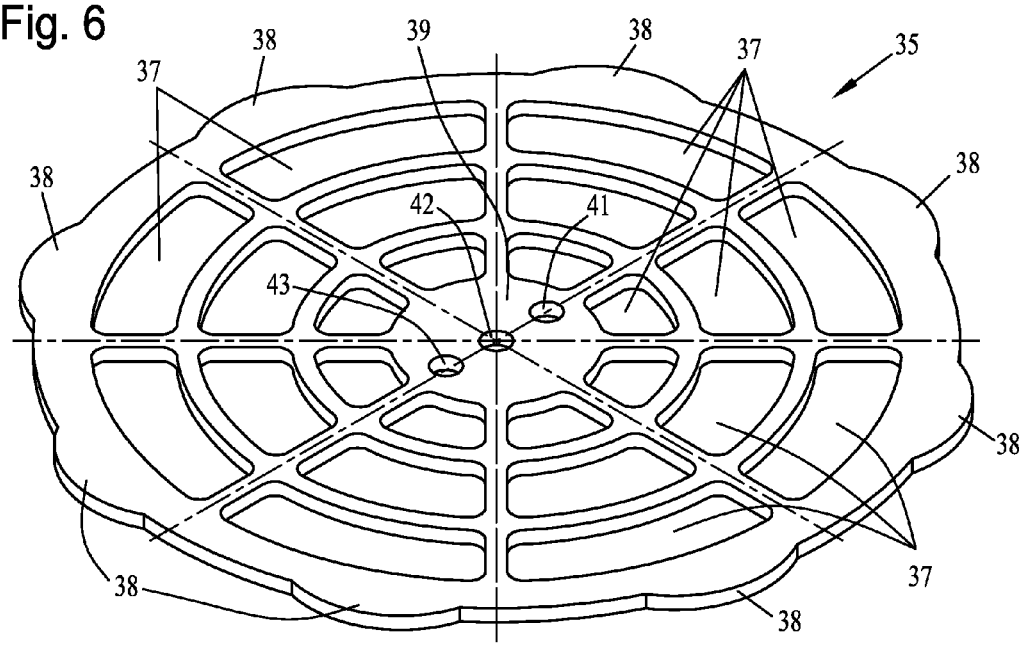
FIG. 6 is a perspective view of a spring washer.

As is evident from FIG. 6, the spring washer 35 is designed as a circular disk, whereby its outer diameter is adapted to the inner diameter of the holding flange 18 of the frame element 15, so that the spring washer 35 can be inserted into the holding flange 18 with little play. The spring washer 35 has a plurality of large-area openings 37, which are arranged uniformly on the circumference and distributed over the radius in the spring washer 35.

Furthermore, a plurality of cam- or tongue-like projections 38, whose number and arrangement on the circumference of the spring washer 35 correspond to the number and arrangement of the insertion expansions 19 of the holding flange 18 of the frame element 15, are provided on the outer circumference of the spring washer 35.

Figure 9:
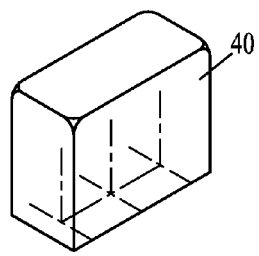
FIG. 9 is a perspective view of a fixed gripping part that can be connected to the spring washer.

Thus, the spring washer 35 with its projections 38 can be inserted into the holding flange 18 of the frame element 15 in a predetermined angular position. In the present exemplary embodiment, a type of holding plate 39, which is used for the fixed fastening of a gripping part 40 (FIG. 9), is provided in the center of the spring washer 35. Accordingly, in the present exemplary embodiment, this holding plate 39 has three through holes 41, 42 and 43, in whose area the gripping part 40 can be placed on the holding plate 39.

The pressure washer 36 is designed in a similar construction as the spring washer 35. The pressure washer 36 also has a plurality of openings 45, which are arranged distributed uniformly in the pressure washer 36 both in the circumferential direction and in the radial direction. The pressure washer 36 likewise has a circular design in its basic structure and on its outer circumference has a plurality of cam- or tongue-like projections 46, which are arranged uniformly distributed and are protruding radially outwards. Also, these projections 46 are arranged on the outer circumference of the pressure washer 36 in their number and arrangement likewise corresponding to the arrangement and number of the insertion expansions 19 of the holding flange 18 of the frame element 15. Thus, the pressure washer 36 can also be inserted fittingly into the holding flange 18 of the frame element 15, whereby the projections 46 mesh with the insertion expansions 19 in a fitting manner or with little play.

For this, it should be noted here that the flange elements 21 defining the respective mounting groove 20 downwards in their thickness correspond approximately to the thickness of the pressure washer 36. I.e., in the state of the pressure washer 36 fully inserted into the frame element 15 fixed to the wall element 3, this pressure washer 36 is held nonrotatably by its projections 46 by means of the flange elements 21 defining the insertion expansions 19.

Figure 7:
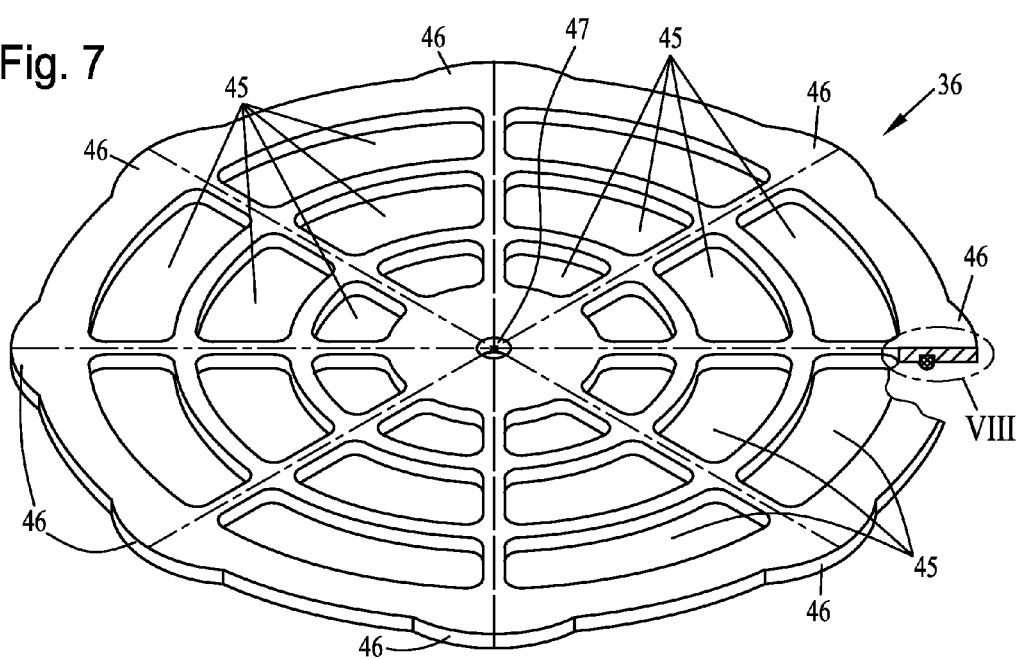
FIG. 7 is a perspective view of a pressure washer.

Further, it is evident from FIG. 7 that the pressure washer 36 has a central through hole 47, which, in the mounted state, runs coaxially to the central through hole 42 of the spring washer 35.

Figure 8:
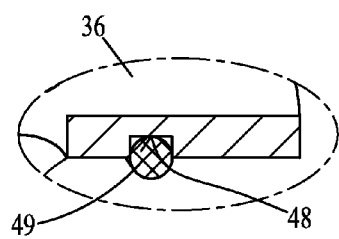
FIG. 8 is an enlarged, perspective detail of the pressure washer from FIG. 7.

Further, the enlarged detail VIII of the pressure washer 36 from FIG. 7 in drawing FIG. 8 shows that on the bottom side the pressure washer 36 is provided with a ring groove 48, in which a sealing ring 49 is mounted circumferentially. With this sealing ring 49, the pressure washer can be placed tightly onto a filter sheet placed in the wall area 4.

The spring washer 35 from FIG. 6 preferably has a slight arch in the center, directed towards the pressure washer 36, so that in the mounted state this presses in a spring-elastic manner against the pressure washer 36 under slight prestress.

Figure 10:
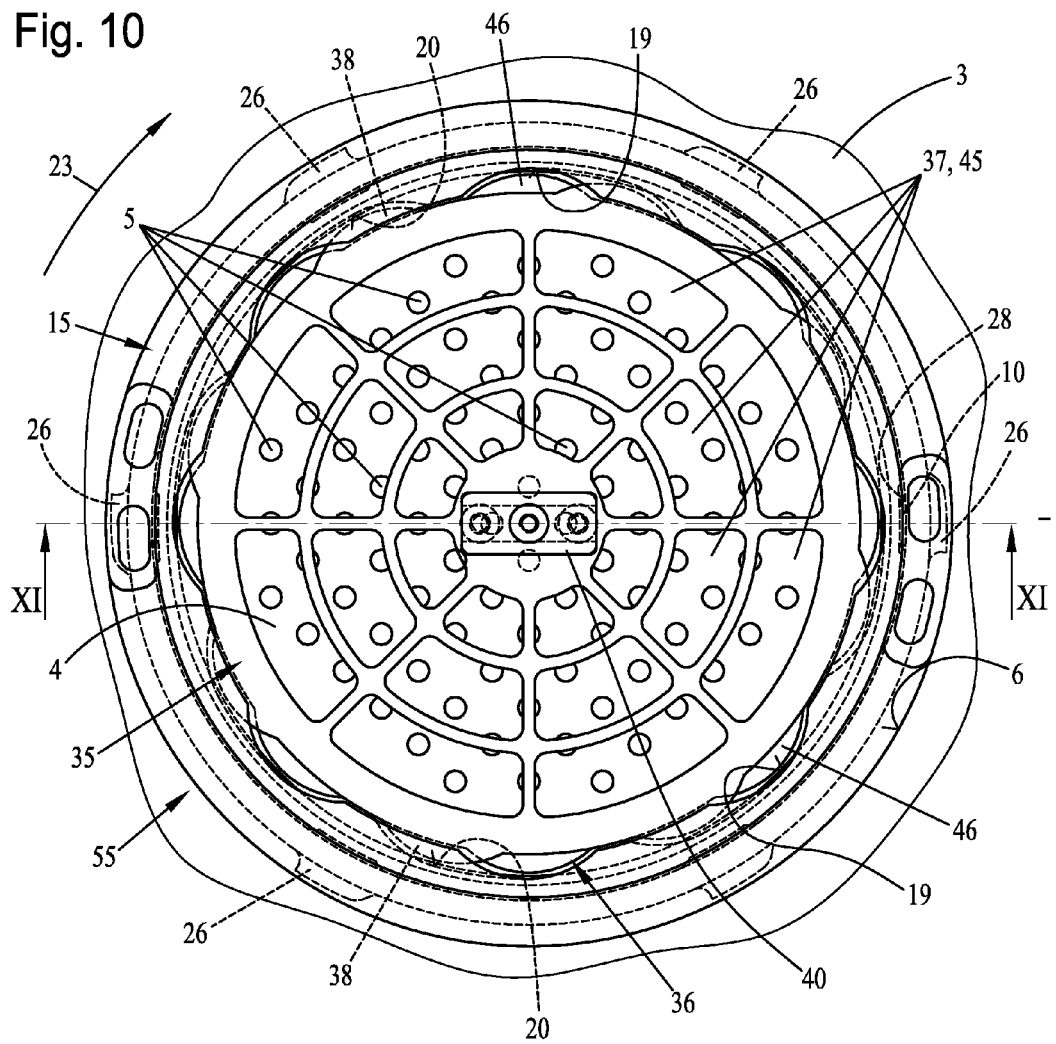
FIG. 10 is a partial view of the container cover with fully mounted filter unit.

FIG. 10 shows a partial top view of the wall element 3 with a fully mounted filter unit 55. It can be seen that the frame element 15 is placed on the wall element 3 and completely surrounds the wall area 4 in a ring-shaped manner. The radial outer centering elements 26 are mounted with extremely little play in the circumferential ring groove 6 of the wall element 3. Furthermore, as a suggestion, it can be seen from FIG. 10 that the radially inward protruding holding flanges 28 mesh with the respectively assigned locking slots 10 of the ring groove 6.

Furthermore, it can be seen that the spring washer as well as the pressure washer 36 are located in the frame element 15. In this mounted position shown in FIG. 10, the openings 37 and 45 of the spring washer 35 and of the pressure washer 36 are arranged congruently. It can be seen that the projections 38 of the spring washer 35 in this mounted state are arranged in the circumferential direction offset to the projections 45 of the pressure washer 36 meshing with insertion expansions 19 and mesh in a positive-locking manner with the respective mounting groove 20. The radial projections 46 of the pressure washer 36 are thus mounted in a fitting manner in the associated insertion expansions 19 of the frame element 15, so that the pressure washer 36 is arranged in the frame element in a nonrotatable manner.

The spring washer 35 was rotated for locking in the direction of arrow 23, so that its radial projections 38 mesh in an axially fixed manner with the respectively assigned mounting groove 20 of the insertion expansions 19.

Furthermore, it can be seen from FIG. 10 that the openings 37 and 45 are arranged in the area of the gas-exchange openings 5 of the wall area 4 and these gas-exchange openings 5 are at least approximately fully released.

FIG. 10 does not show the filter sheet located between the pressure washer 36 and the wall area 4, so that the gas-exchange openings 5 can correspondingly be seen.

Furthermore, it is evident from FIG. 10 that the gripping part 40 on the top side is mounted on the spring washer 35, so that the spring washer 35 can be rotated via this gripping part 40 in a simple manner for "locking" and "unlocking."

Figure 11:
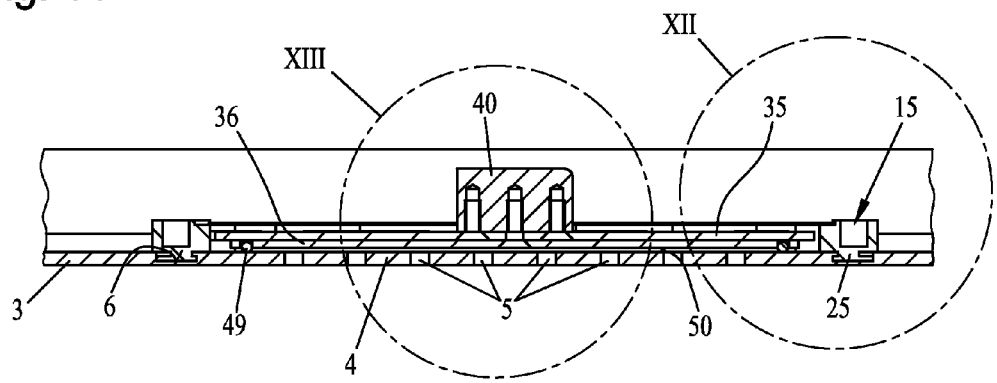
FIG. 11 is a partial section XI-XI of the container cover from FIG. 10 with fully mounted filter unit.

For this, FIG. 11 shows a sectional view XI-XI from FIG. 10. It can be seen that the gripping part 40 is mounted in a fixed manner on the top side on the spring washer 35. The pressure washer 36 is arranged between the spring washer 35 and the wall element 3 or its wall area 4. On the top side, the sealing ring 49 lies tightly on the filter sheet 50, which can be seen as a suggestion. Here the filter sheet 50 completely covers the gas-exchange openings 5.

Furthermore, the frame element 15, with its lower ring land 25, meshes with the ring groove 6 of the wall element 3. For this, FIG. 12 shows an enlarged detail XII from FIG. 11. It can be seen that the frame element 15 is mounted in a fitting manner in the ring groove 6 with its radially outwardly protruding centering elements 26 of the ring land 25. The radially inwardly protruding holding flange 28 of the circumferential ring land 25 meshes with the respectively assigned locking slot 10 in a fixed manner.

Figure 12:
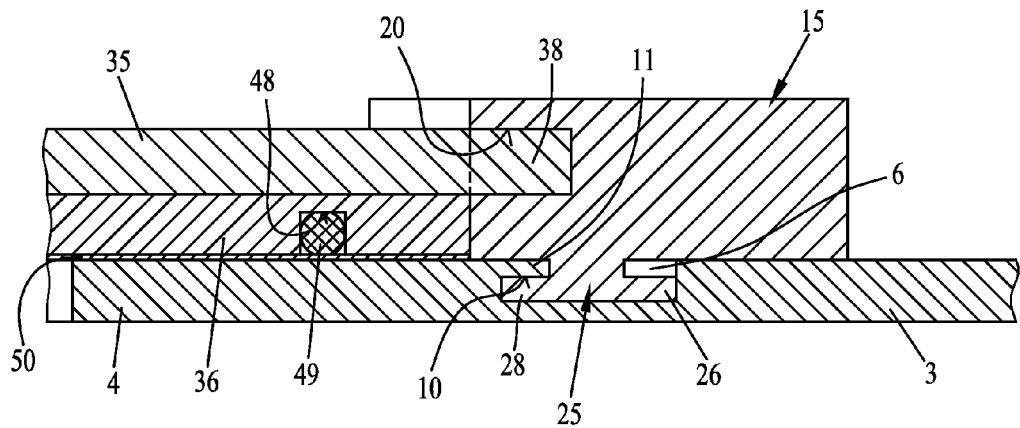
FIG. 12 is an enlarged detail XII of the container cover from FIG. 11 in the area of the connection of the frame element to the container cover.

Furthermore, it can be seen from FIG. 12 that the filter sheet 50 is mounted between the pressure washer 36 and the wall element 3 or wall area 4. Here the sealing ring 49 presses axially against the filter sheet 50, so that this lies tightly on the wall element 3. Accordingly, the radial projection 38 of the spring washer 35 meshes with the assigned mounting groove 20 of the frame element 15, so that the pressure washer 36 with its sealing ring 49 is pressed against the filter sheet 50. Thus, due to the spring-elastic design of the spring washer 35 and also of the sealing ring 49, a sealing of the wall area 4 with the placed filter sheet 50 is especially produced against the frame element 15.

Figure 13:
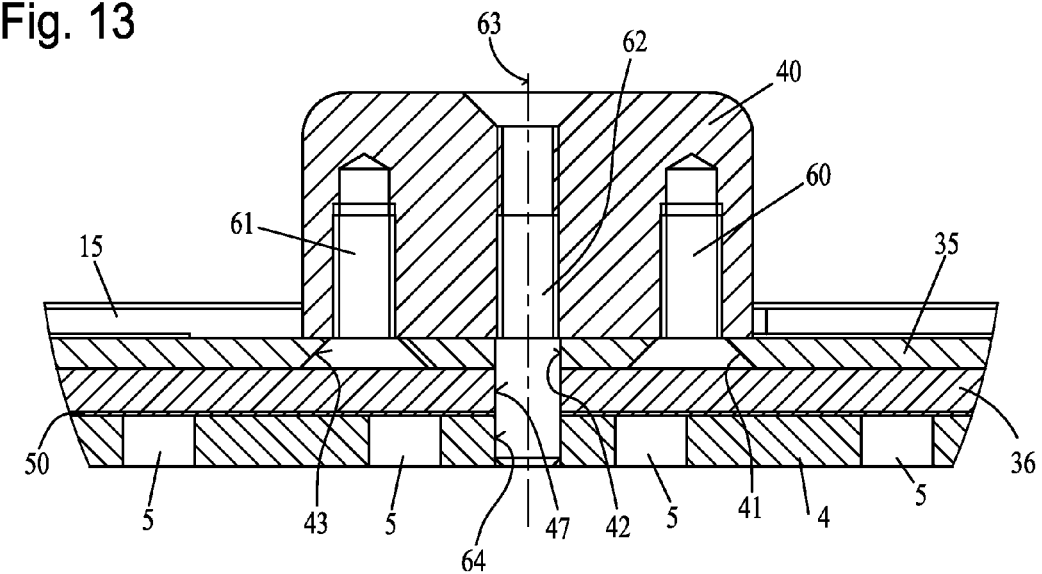
FIG. 13 is an enlarged detail XIII of the container cover from FIG. 11 in the area of the connection of the gripping part to the spring washer.

Furthermore, FIG. 13 shows in an exemplary manner an enlarged view XIII from FIG. 11, from which can be seen especially the manner in which the gripping part 40 is fastened to the top side of the spring washer 35. The gripping part 40 is fastened to the spring washer 35 by means of two mounting screws 60 and 61. Accordingly, these two mounting screws 60 and 61 project through the through holes 41 and 42 already mentioned in regard to FIG. 6. Furthermore, a centering pin 62, which represents a common axial connection for the spring washer 35 and the pressure washer 36 and accordingly projects in the central through holes 42 and 47 thereof, is screwed into the gripping part 40. This centering pin 62 is designed in its length in such a way that it furthermore meshes with a central hole 64 of the wall area 4 and accordingly also projects through the filter sheet 50. Thus, by means of this centering pin 62, the filter sheet 50, pressure washer 36 and spring washer 35 are held rotatably concentric to the ring groove 6 and thus to the frame element 15 meshing with this ring groove 6. The filter sheet 50 here covers the gas-exchange openings 5 in the wall area 4 of the wall element 3 and is held on the surface of the wall area 4 by the pressure washer 36, which can likewise be seen in FIG. 3.

Figure 14:
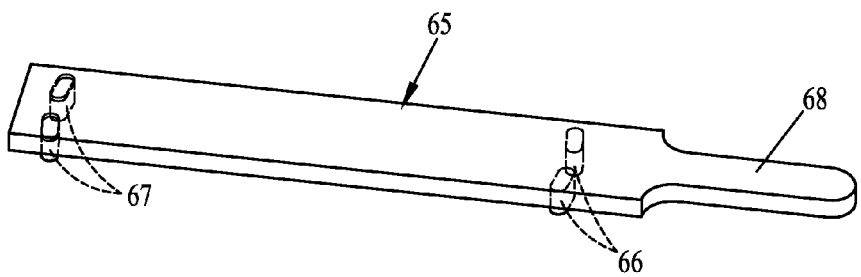
FIG. 14 is a perspective view of a hand lever that can be coupled with the frame element in a nonrotatable manner.

FIG. 14 shows in an exemplary manner an embodiment variant of a hand lever 65 that is provided for establishing and canceling the bayonet connection between the frame element 15 and the wall element 3. For this, the hand lever 65 has, on the bottom side, two contact pins 66 and 67 arranged in pairs, which can be meshed in a positive-locking manner with the positive-locking elements 16 and 17 (FIG. 3) arranged on the top side in the frame element 15. Furthermore, it can be seen from FIG. 14 that the hand lever 65 has on the inside at least one gripping element 68, by means of which the correspondingly necessary torque can be applied for establishing the bayonet connection or for canceling the bayonet connection.

While specific embodiments of the invention have been shown and described in detail to illustrate the application of the principles of the invention, it will be understood that the invention may be embodied otherwise without departing from such principles.

What is claimed is:

1. A medical sterilization container comprising:
   a removable container cover having a wall area provided with gas-exchange openings; and
   a filter unit for gas exchange, the filter unit comprising:
   an interchangeable filter sheet covering the gas-exchange openings on an inside;
   a pressure washer provided with openings;
   a ring-shaped circumferential frame element having bayonet catch elements, the filter sheet being arranged within the ring-shaped circumferential frame element and being held pressably against an inside of the wall area by the pressure washer, whereby the pressure washer is detachably connected to the frame element or to the wall area and has a ring groove with an elastic sealing ring, the sealing ring sealing the wall area against the frame element; and
   a spring washer, the pressure washer being pressed by the spring washer against the wall area, the spring washer being provided with bayonet connection elements, which can be meshed and unmeshed with the bayonet catch elements of the frame element, the spring washer being rotatable opposite the pressure washer about a common central axis of rotation of the pressure washer and of the spring washer.

2. A medical sterilization container in accordance with claim 1, wherein the spring washer is provided with openings, which are designed and arranged according to a same pattern as a pattern of the openings of the pressure washer.

3. A medical sterilization container in accordance with claim 1, wherein the bayonet connection elements of the spring washer are formed from projections protruding radially outwardly on a circular circumference thereof, which mesh with radial mounting slots or grooves arranged on an inside of the frame element, which are each connected to insertion expansions of the frame element in a direction of rotation.

4. A medical sterilization container in accordance with claim 3, wherein:
   the insertion expansions extend over an entire height or thickness of the frame element; and
   the pressure washer is provided on a circumference thereof with radially outwardly protruding, projections, each mounted in one of the insertion expansion to secure the pressure washer against rotation.

5. A medical sterilization container in accordance with claim 1, wherein the frame element has a circumferential ring land protruding axially towards the wall area, the ring land meshing with a ring groove of the wall area and being detachably connected to the ring groove via a bayonet connection.

6. A medical sterilization container in accordance with claim 1, wherein the pressure washer and the spring washer are the same size and are formed of metal or plastic and lie on top of one another within the frame element with an congruent position of the openings of the pressure washer and the spring washer.

7. A medical sterilization container in accordance with claim 1, wherein the spring washer in the mounted state lies axially elastically on the pressure washer and is concentrically rotatably centered on the spring washer by means of a central axial connection.

8. A medical sterilization container in accordance with claim 1, wherein the spring washer is provided on a top side with at least one fixed gripping part.

9. A medical sterilization container in accordance with claim 2, further comprising a manually actuatable hand lever wherein:
   the ring-shaped frame element is provided on a top side with at least two diametrically opposed positive-locking elements; and
   the manually actuatable hand lever is nonrotatably and detachably meshed in a positive-locking manner with the positive-locking elements of the frame element.

10. A medical sterilization container in accordance with claim 3, further comprising a manually actuatable hand lever wherein:
    the ring-shaped frame element is provided on a top side with at least two essentially diametrically opposed positive-locking elements; and
    the manually actuatable hand lever is nonrotatably and detachably meshed in a positive-locking manner with the positive-locking elements of the frame element.

11. A medical sterilization container comprising:
    a container cover having a wall area with gas-exchange openings;
    a gas exchange filter sheet covering the gas-exchange openings on an inside;
    a pressure washer provided with openings;
    a ring-shaped circumferential frame element having bayonet catch elements, the filter sheet being arranged within the ring-shaped circumferential frame element and being held pressably against an inside of the wall area by the pressure washer, whereby the pressure washer is detachably connected to the frame element or to the wall area and has a ring groove with an elastic sealing ring, the sealing ring sealing the wall area against the frame element; and
    a spring washer, the pressure washer being pressed by the spring washer against the wall area, the spring washer being provided with bayonet connection elements for being meshed and unmeshed with the bayonet catch elements of the frame element, the spring washer being rotatable opposite the pressure washer about a common central axis of rotation of the pressure washer and of the spring washer.

12. A medical sterilization container in accordance with claim 11, wherein the spring washer is provided with openings, which are designed and arranged according to a same pattern as a pattern of the openings of the pressure washer.

13. A medical sterilization container in accordance with claim 11, wherein the bayonet connection elements of the spring washer are formed from projections protruding radially outwardly on a circular circumference thereof, which mesh with radial mounting slots or grooves arranged on an inside of the frame element, which are each connected to insertion expansions of the frame element in a direction of rotation.

14. A medical sterilization container in accordance with claim 13, wherein:
    the insertion expansions extend over an entire height or thickness of the frame element; and
    the pressure washer is provided on a circumference thereof with radially outwardly protruding, projections, each mounted in one of the insertion expansion to secure the pressure washer against rotation.

15. A medical sterilization container in accordance with claim 11, wherein the frame element has a circumferential ring land protruding axially towards the wall area, the ring land meshing with a ring groove of the wall area and being detachably connected to the ring groove via a bayonet connection.

16. A medical sterilization container in accordance with claim 11, wherein the pressure washer and the spring washer are the same size and are formed of metal or plastic and lie on top of one another within the frame element with an congruent position of the openings of the pressure washer and the spring washer.

17. A medical sterilization container in accordance with claim 11, wherein the spring washer in the mounted state lies axially elastically on the pressure washer and is concentrically rotatably centered on the spring washer by means of a central axial connection.

18. A medical sterilization container in accordance with claim 11, wherein the spring washer is provided on a top side with at least one fixed gripping part.

19. A medical sterilization container in accordance with claim 12, further comprising a manually actuatable hand lever wherein:
   the ring-shaped frame element is provided on a top side with at least two diametrically opposed positive-locking elements; and
   the manually actuatable hand lever is nonrotatably and detachably meshed in a positive-locking manner with the positive-locking elements of the frame element.

20. A medical sterilization container in accordance with claim 13, further comprising a manually actuatable hand lever wherein:
   the ring-shaped frame element is provided on a top side with at least two diametrically opposed positive-locking elements; and
   the manually actuatable hand lever is nonrotatably and detachably meshed in a positive-locking manner with the positive-locking elements of the frame element.

* * * * *